United States Patent [19]

Varelis et al.

[11] Patent Number: 5,033,474
[45] Date of Patent: Jul. 23, 1991

[54] ECG CABLE STORAGE MEANS IN A PERSONAL HEALTH MONITOR

[75] Inventors: James S. Varelis, Chicago; William Fang, Naperville, both of Ill.

[73] Assignee: Buddy Systems, Inc., Northbrook, Ill.

[21] Appl. No.: 461,248

[22] Filed: Jan. 5, 1990

[51] Int. Cl.⁵ ............................................. A61B 5/02
[52] U.S. Cl. .............................. 128/696; 191/12.2 R; 128/670; 128/695; 362/387
[58] Field of Search ..................... 128/695, 696, 670; 364/413.02–413.06; 242/16; 191/12.2 R; 362/387; 606/32, 34

[56] References Cited

U.S. PATENT DOCUMENTS

| | | | |
|---|---|---|---|
| 3,099,398 | 7/1963 | Croteau | 362/387 |
| 3,592,157 | 7/1971 | Schwartz | 362/387 |
| 3,628,133 | 12/1971 | Dornberger | 191/12.2 R |
| 3,733,478 | 5/1973 | Barker | 240/2 |
| 3,821,496 | 6/1974 | Malone | 191/12.2 R |
| 4,583,553 | 3/1986 | Shah et al. | 128/704 |
| 4,731,726 | 3/1988 | Allen, III | 364/416 |
| 4,803,625 | 2/1990 | Fu et al. | 364/413.03 |

Primary Examiner—Francis Jaworski
Assistant Examiner—George Manuel
Attorney, Agent, or Firm—Willian Brinks Olds Hofer Gilson & Lione

[57] ABSTRACT

In a personal health monitor that includes one or more cables for connection to a patient information about whose clinical condition the personal health monitor can monitor, an improvement for the storage of one or more cables. The improvement includes a spool with a shank portion about which a cable can be wound and a head portion at the end of the shank portion and larger in dimension than the shank portion so as to retain the cable on the shank portion whereby tangling of the cable can be prevented. In an aspect of a further embodiment, a fastener on the head portion secures an end of the cable when not in use thereby preventing tangling. Additionally, in an aspect of a still further embodiment, the spool can be mounted on a bracket that is removably secured to the inside of a compartment door which when open represents the spool with its cable for use by the patient.

18 Claims, 2 Drawing Sheets

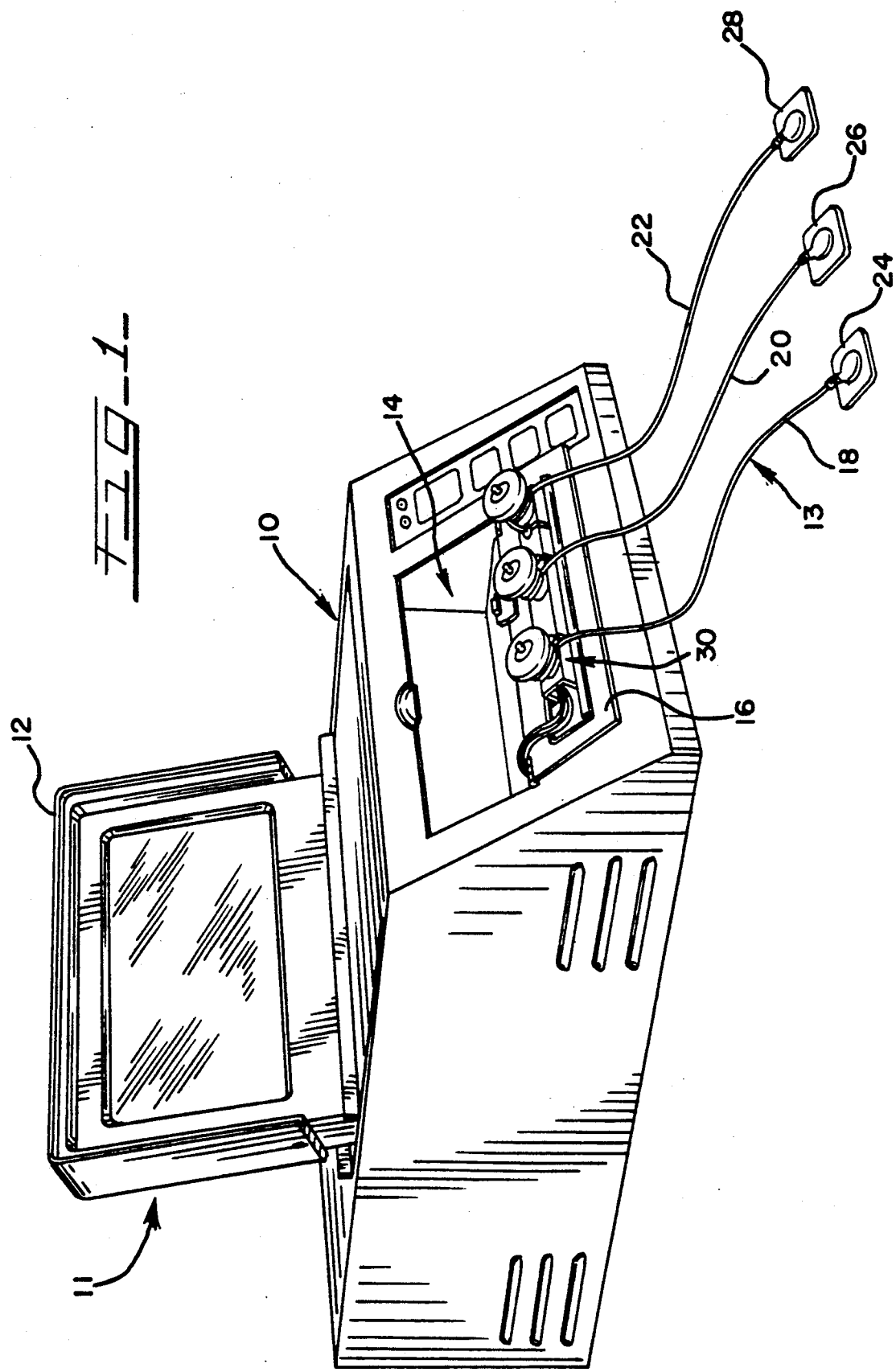

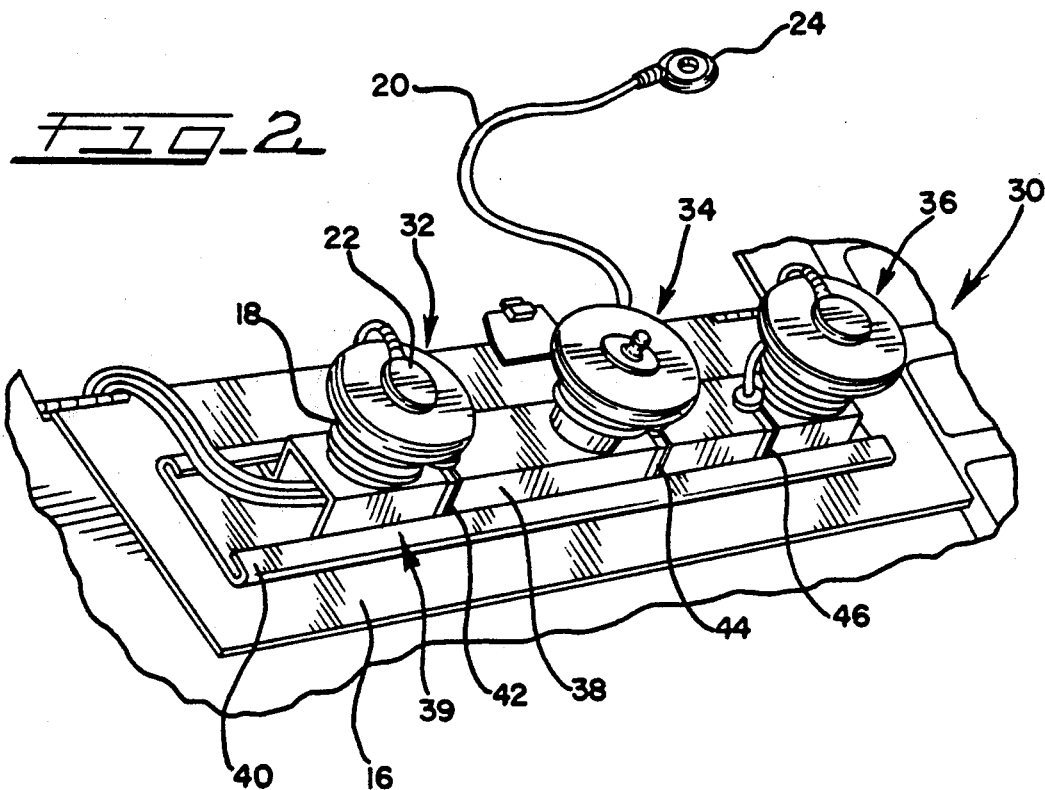
FIG_2
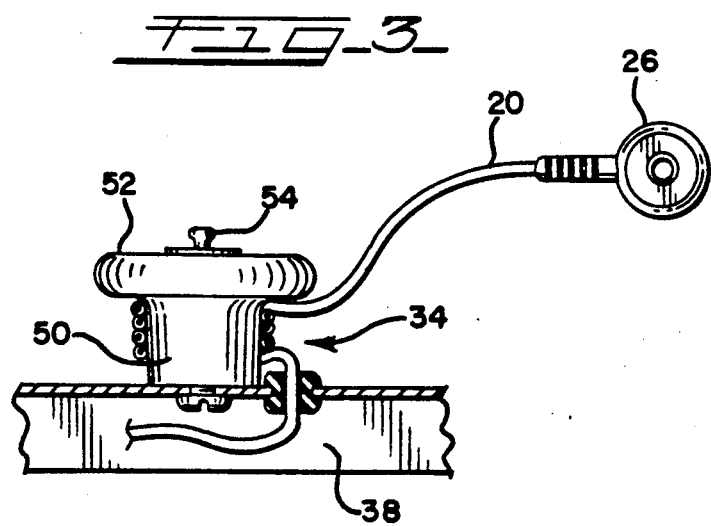
FIG_3

ECG CABLE STORAGE MEANS IN A PERSONAL HEALTH MONITOR

BACKGROUND OF THE INVENTION

This invention relates to personal health monitors and more particularly to improvements for a personal health monitor for the storage of cables.

A personal health monitor is a device used to measure and record one or more clinical parameters of a patient for later transmission to the patient's physician or other health care provider. The personal health monitor may be used in a hospital or clinical setting as an adjunct to existing care. However, the personal health monitor may also be used by the patient himself in his own home. When used by a patient in his own home, the patient operates the personal health monitor to record certain of his own clinical parameters for subsequent transmission by the personal health monitor to the patient's physician or other health care provider. The personal health monitor, therefore, may be used by the patient who has a condition requiring monitoring of one or more clinical parameters but who otherwise does not require the level of care such as provided by a hospital. In such a circumstance, the personal health monitor provides potential savings in medical costs involved with a hospital stay. A personal health monitor of the type considered herein is described more fully in U.S. Pat. No. 4,803,625.

The personal health monitor may include one or more test components, or sensors, a programmable computer such a general purpose personal computer, and an interface connecting the sensors with the personal computer. In the above mentioned patent, the prograammable computer is a laptop personal computer having a display screen, keyboard, CPU (central processing unit), disk drive, and a means for connecting to the sensor interface to exchange data, such as by a port, bus, interface card, or other means.

A program on the computer affords an interactive, user-friendly way for the patient to interact with the personal health monitor to measure one or more clinical parameters. For purposes of this application, clinical parameters include physiological parameters, (such as vital signs like ECG, blood pressure, temperature, and weight), medication compliance and volunteered patient replies. The program can be specifically tailored to the patient's individual needs.

With the sensors a patient can measure one or more specific physiological parameters. The interface connects to the sensors and converts the signals from the sensors for storage as data by the personal computer. The personal computer can later transmit the data for review by the patient's physician or other health care provider.

In accordance with the testing regime established by the patient's physician, the personal health monitor may be used on a specific schedule to conduct sessions to measure certain of the patient's clinical parameters following instructions provided by the personal health monitor. In the embodiment described in the above referenced patent, the personal health monitor includes a personal computer with a display screen portion that can provide instructions for conducting a session in which clinical parameters are determined. For example, the program on the personal computer can provide instructions for measuring a patient's blood pressure or ECG. In addition, the personal health monitor can also present the patient with a series of questions about his health and prompt the patient for responses. For example, the patient can be asked to volunteer replies in response to a structured series of questions (e.g., "Do you have a fever?" followed by "If so, is your fever continuous or intermittent?"). The personal health monitor can be programmed to sound a reminder to initiate a testing session and record whether the patient adheres to the established schedule.

The personal health monitor can be used to give the patient instructions for taking medicines and provide the patient with reminders to take medications. Moreover, the personal health monitor can allow a physician to readily modify a medication schedule. For example, based upon the physiological parameters gathered by the personal health monitor and reviewed by a patient's physician, the physician may decide to alter the medication.

As described in the above referenced patent, the personal health monitor may include means for data storage so that the clinical parameters measured can be stored as data. The personal computer may include a modem so that the data can be transmitted to a central station. The data transmission can be done automatically by a program on the personal computer. The physician or other health care provider can then obtain the information from the central station either by calling, downloading or other means of communication. Alternately, a health care provider may be able to access the personal health monitor directly.

An advantage of the personal health monitor is that a high level of patient surveillance can be provided, even with the patient outside of a hospital or other expensive facility. Thus, the personal health monitor has the capability of lowering health care costs while at the same time maintaining or even improving the level of patient surveillance. Additional benefits include being able to return a patient to his home environment sooner and also providing a means for involving the patient in his own health program.

In order to make the advantages of the personal health monitor available to a wide variety of patients undergoing different types of medical supervision and having varying levels of familiarity with diagnostic equipment, it is important to provide a user-friendly interface that is easy to use. Instructions provided on the display screen portion of the personal health monitor should be easy to understand and the test equipment should not be intimidating. Moreover, the equipment used in the testing of the physiological parameters should be easy to store when not in use yet easy to set up and use by the patient for a session of testing.

Typically, the devices used to test the physiological parameters are connected to the interface by cables or leads. A patient may be intimidated or confused when confronted by a maze of cables attached to a unfamiliar device. The patient may become especially confused if several of the cables are similar in appearance.

As an example, in a session with a personal health monitor in which a patient's ECG is taken, three cables are affixed to a patient's body: one lead on the inside of each arm and one lead on the patient's leg. The cables are affixed to a patient's body by means of disposable, conductive self-adhesive pads. The other ends of the ECG cables terminate in a plug that can be inserted in a jack connected to the interface to the computer. The cables must be of a sufficient length so that they can reach to a patient that may be seated or standing in front of the monitor. Typically, each lead can be as long as four feet. After testing and when not in use the cables should be stored for the next session. It can present a problem for the patient if the cables become tangled or mixed up. In such an vent, the patient may be discouraged from using the personal health monitor. Further, if the cables become tangled or mixed, they can become damaged or switched thus preventing the personal health monitor from acquiring valid data and possibly requiring a service call.

Accordingly, it is an object of the present invention to provide a user-friendly, efficient and neat means for storage for sensor cables in a personal health monitor.

It is another object of the present invention to prevent entanglement of sensor cables in a personal health monitor.

It is yet another object of the present invention to provide neat and easy-to-use storage for sensor cables in a personal health monitor.

It is still yet another object of the present invention to provide an easy-to-use storage for sensors cables in a personal health monitor that will be used repeatedly or periodically in sessions with a patient.

Another object of the present invention is to provide in a personal health monitor easy-to-understand identification for a multiplicity of sensor cables.

Yet another object of the present invention is to provide in a personal health monitor easy-to-understand storage and identification for a multiplicity of ECG cables.

Still another object of the present invention is to provide for storage of ECG cables in a personal health monitor when not in use.

A further object of the present invention is to provide in a personal health monitor for storage and use of ECG cables and to prevent entanglement of ECG cables when in use especially where sufficient lengths of ECG cables must be provided to accommodate in home use.

A yet further object of the present invention is, in a personal health monitor that includes sensors for taking an ECG, to provide for securing the cables for neat and efficient storage utilizing existing fasteners on the cables.

SUMMARY OF THE INVENTION

To achieve the foregoing and other objectives and in accordance with the purposes of the present invention, as embodied and broadly described herein, the present invention provides an improvement for the storage of cables with a personal health monitor. In a personal health monitor that includes one or more cables for connection to sensors used to measure one or more clinical parameters of a patient, the present invention provides an improvement comprising a spool with a shank portion about which a cable can be wound and a head portion at the end of the shank portion and larger in dimension than the shank portion so as to retain the cable on the shank portion whereby tangling of the cable can be prevented.

BRIEF DESCRIPTION OF THE DRAWINGS

FIG. 1 is a perspective view of a personal health monitor that incorporates a preferred embodiment of this invention.

FIG. 2 is a perspective view of the ECG cable storage means included in the embodiment of the invention depicted in FIG. 1.

FIG. 3 is a side view of one spool as mounted on the bracket in the storage means depicted in FIG. 2.

DETAILED DESCRIPTION OF THE PREFERRED EMBODIMENT

Referring to FIG. 1, there is shown a personal health monitor 10, such as may be used by a patient to monitor one or more clinical parameters of the patient for subsequent review by the patient's physician or other health care provider. The personal health monitor 10 includes a personal computer 11 having a display screen 12 whereby instructions or prompts can be given about measuring a patient's clinical parameters, including vital signs, medications taken, and volunteered information about his condition, as described above. In the preferred embodiment, the personal computer is a Tandy model 1400 Laptop. Personal health monitor 10 includes one or more sensors 13 for measuring one or more physiological parameters of the patient. These sensors 13 connect to the personal health monitor 10 inside sensor compartment 14 and may be contained in sensor compartment 14 of personal health monitor 10 when not in use. Physiological parameters of the patient that can be measured by these sensors include blood pressure, temperature, and ECG, for example. These sensors 13 are similar to the devices that would normally be used to measure these physiological parameters except that sensors 13 are connected by wires or cables to an interface (not shown) inside the personal health monitor 10. The interface converts the measurements taken by the sensors 13 into signals that can be stored as data by the computer 11 of the personal health monitor 10. The sensors 13 depicted in FIG. 1 may terminate in a plug on the end that connects to a jack in the sensor compartment 14 which in turn connects to the interface inside the personal health monitor 10. Alternately, the sensors 13 can be wired directly to the interface.

Shown in FIG. 1 are sensors 13 for taking a patient's ECG. These sensors 13 include cables 18, 20 and 22. Cables 18, 20 and 22 are connected to conductive self-adhesive pads 24, 26 and 28, respectively. Pads which may be used are the SynCor brand pad. On one side of pads 24, 26 and 28 are snap-type fasteners (such as dot snappers) which attach to corresponding snap-type fastener receptors on cables 18, 19 and 22, respectively. On the other side of pads 24, 26 and 28 are peel-off strips that can be removed to expose an adhesive surface that will adhere to the patient's body for the taking of an ECG test. Pads 24, 26 and 28 are disposable and are discarded after use by the patient.

In the preferred embodiment, the cables are different colors so that the patient can readily identify the different cables. In the preferred embodiment, cable 18 is green and intended to be attached to the patient's body on the inner left leg just above the ankle. Cable 20 which is black is intended to be attached to the patient on the inner part of the patient's left arm. Cable 22 which is white is intended to be attached to the patient on the inner part of the patient's right arm. When not in use, cables 18, 20 and 22 and any other sensors are placed in sensor compartment 14. Compartment 14 may be closed with compartment door 16 when the sensors 13 are not in use.

Cables 18, 20 and 22 may be from two to four feet in length to accommodate attaching to a patient's body. It can readily be appreciated that ECG cables 18, 20 and 22 can become tangled with each other and with cables for other sensors, especially during storage in compartment 14 of personal health monitor 10. To provide for ease of use and storage of the sensor cables, the present invention provides a means for cable storage 30. In the preferred embodiment, cable storage means 30 is located on the interior side of compartment door 16. Compartment door 16 is attached to the personal health monitor 10 by hinges along its lower edge so that compartment door 16 will remain open and stationary when in the open position thereby allowing ready access by the patient to the cable storage means 30. Compartment door 16 may be made of the same material as the personal health monitor enclosure (plastic or metal).

Referring to FIG. 2, there is depicted a view of the cable storage means 30 mounted on compartment door 16. Spools 32, 34 and 36 are affixed to bracket 38. Bracket 38 is elongated and U-shaped to accommodate feeding of the cables beneath it between bracket 38 and the compartment door 16. Bracket 38 includes flanges which engage channels 39 on the interior of compartment door 16. Accordingly, bracket 38 can slidably be removed from compartment door 16 for the purpose of replacing the ECG cables or for replacing the bracket with a bracket having a different number or type of cables. Bracket 38 contains slots 42, 44 and 46 to accommodate threading cables 18, 20 and 22, respectively, to the underside of bracket 38.

Referring to FIG. 3, there is shown a view of spool 34 which contains the black cable used for attachment to a patient's left arm. The description of spool 34 can be understood to apply to spools 32 and 36 as well inasmuch as spools 32 and 36 are of similar construction. In the preferred embodiment, spool 34 is made of plastic, but it may be made of any relatively firm material such as metal or ceramic. Spool 34 is attached to bracket 38 by a fastening means such as a screw (not shown). Spool 34 has a shank portion 50 which is generally cylindrical in shape so that ECG cable 20 can be wound about it. Spool 34 has an enlarged head 52 at the end opposite where spool 34 is attached to bracket 38. The enlarged head 52 serves to prevent ECG cable 20 from slipping off of the shank portion 50 of spool 34.

To provide for the securing of the cable end during storage or when the cable is not in use, a fastener 54 is associated with the spool 34. Fastener engages the free end of cable 20 so that it does not unwind off of spool 34. In the preferred embodiment, fastener 54 is a snap-type and is affixed to the top of enlarged head 52 of spool 34. Snap-type fastener use in the preferred embodiment is similar to the snap-type fastener used on the disposable adhesive pads that the patient sticks to his arms and leg. Accordingly, when ECG cable 20 is wound about spool 34 for storage when not in use, the end of ECG cable 20 may be neatly secured by snapping the receptor end 26 of ECG cable 20 onto fastener 54. Frictional contact between snap-type fastener 54 and receptor 26 is normally sufficient to prevent ECG cable 20 from unwinding on spool 34 thereby preventing tangling of the cable. Fastener 54 may be of a type other than a snap-type fastener if, for example, the cable does not already possess a complementary fastener receptor on it such as if the cable is used for connection to a different type of sensor. Then a different type of fastener may be used such as a hook or clip.

It is therefore intended that the foregoing detailed description be regarded as illustrative rather than limiting, and that it be understood that it is the following claims, including all equivalents, which are intended to define the scope of the invention.

I claim:

1. In a personal health monitor that includes a cable for connection to a sensor capable of measuring a clinical parameter of a patient, an improvement comprising:
   a spool comprising:
   a shank portion about which a cable can be wound and having a first end thereof fixed to the personal health monitor, and
   a head portion at a second end of said shank portion and larger in dimension than said shank portion so as to retain the cable on said shank portion.

2. The personal health monitor improvement of claim 1 including:
   a fastener for releasably securing a free end of the cable adjacent to said shank portion of said spool.

3. The personal health monitor improvement of claim 2 wherein said fastener is located on said head portion of said spool.

4. The personal health monitor improvement of claim 3 in which the personal health monitor includes a compartment therein for the storage of the cable, and further in which the personal health monitor improvement further comprises:
   a door for access to the compartment, and further wherein said spool is attached to an inside surface of said door.

5. The personal health monitor improvement of claim 4 further comprising:
   a bracket upon which said spool is connected, and further in which said bracket is removably secured to said inside surface of said door.

6. The personal health monitor improvement of claim 5 in which said bracket is U-shaped to accommodate feeding cable between said bracket and the door.

7. The personal health monitor improvement of claim 6 in which said door includes channels and in which said bracket further comprises flanges and further wherein said bracket is removably secured to the door by engaging said flanges in the channels.

8. The personal health monitor improvement of claim 7 in which said bracket has a slot adjacent where said spool is connected to said bracket whereby a cable wound on said spool can pass to the underside of said bracket through the slot.

9. The personal health monitor improvement of claim 7 in which the cable is capable of connecting the personal health monitor to a patient for the purpose of taking an ECG of the patient, and further in which one end of the cable includes a snap-type fastener for releasably connecting to a complementary snap-type fastener receptor on an adhesive pad that can be affixed to the patient and further in which said fastener further comprises a snap-type fastener receptor.

10. The personal health monitor improvement of claim 9 including a second spool and a third spool connected to the personal health monitor.

11. In a personal health monitor of the type having a plurality of ECG cables for connection to respective ECG electrodes, wherein each of the ECG cables terminates in a respective first snap fastener, the improvement comprising;
   a plurality of fixed spools each spool having a shank portion about which a respective one of the cables can be wound and a head portion at an end of said shank portion and larger in dimension than said shank portion so as to retain the respective cable on said shank portion, and a plurality of second snap fasteners for releasably securing respective ones of the first snap fasteners, said second snap fasteners connected to said head portions of said spools.

12. The improvement of claim 11 in which the personal health monitor includes a door for access to a compartment therein for the storage of one or more cables, and further wherein said plurality of spools is attached to an inside surface of said door.

13. In a personal health monitor that includes a cable for connection to a sensor capable of measuring a clinical parameter of a patient whose condition the personal health monitor can monitor, an improvement comprising:
    a spool including:
        a shank portion about which the cable can be wound, said shank portion connected at a first end thereof to the personal health monitor,
        a head portion at another end of said shank portion and larger in dimension than said shank portion so as to retain the cable on said shank portion, and
        a fastener located on said head portion for releasably securing a free end of the cable when not in use adjacent to said shank portion of said spool.

14. The personal health monitor improvement of claim 13 in which the personal health monitor includes a compartment therein for the storage of the cable, and further in which the personal health monitor improvement further comprises:
    a door for access to the compartment, and further wherein said spool is attached to an inside surface of said door.

15. The personal health monitor improvement of claim 13 in which the cable is capable of connecting the personal health monitor to a patient for the purpose of taking an ECG of the patient, and further in which one end of the cable includes a snap-type fastener for releasably connecting to a complementary snap-type fastener receptor on an adhesive pad that can be affixed to the patient and further in which said fastener located on said head portion further comprises:
    a snap-type fastener receptor compatible with the snap-type fastener on one end of the cable.

16. In a personal health monitor that includes a cable for connection to a sensor capable of measuring a clinical parameter of a patient whose condition the personal health monitor can monitor, a compartment in the personal health monitor for the storage of the cable, and a closable door for access to the compartment, an improvement comprising:
    a spool having:
        a shank portion about which the cable can be wound, said shank portion connected at a first end thereof to an inner side of the closable door, and
        a head portion connected to a second end of said shank portion said second end opposite said first end, said head portion larger in dimension than said shank portion so as to retain the cable on said shank portion.

17. The personal health monitor improvement of claim 16 further comprising:
    a fastener on said head portion and capable of connecting to an end of the cable.

18. The personal health monitor improvement of claim 16 in which one end of the cable includes a snap-type fastener for releasably connecting to a complementary snap-type fastener receptor on an adhesive pad that can be affixed to the patient and further in which said fastener located on said head portion further comprises:
    a snap-type fastener receptor compatible with the snap-type fastener on one end of the cable.

* * * * *

UNITED STATES PATENT AND TRADEMARK OFFICE
CERTIFICATE OF CORRECTION

PATENT NO. : 5,033,474
DATED : July 23, 1991
INVENTOR(S) : James S. Varelis et al.

Page 1 of 2

It is certified that error appears in the above-identified patent and that said Letters Patent is hereby corrected as shown below:

<u>IN THE ABSTRACT</u>

On the cover page, line 16 of the Abstract, please delete "represents" and substitute therefor --presents--.

In column 1, line 32, after "such" please insert --as--.

In column 1, line 35, please delete "prograammable" and substitute therefor --programmable--.

In column 2, line 57, before "unfamiliar" please delete "a" and substitute therefor --an--.

In column 3, line 6, please delete "vent" and substitute therefor --event--.

In column 3, line 22, please delete "sensors" and substitute therefor --sensor--.

In column 4, line 45, please delete "19" and substitute therefor --20--.

UNITED STATES PATENT AND TRADEMARK OFFICE
CERTIFICATE OF CORRECTION

PATENT NO. : 5,033,474
DATED : July 23, 1991
INVENTOR(S) : James S. Varelis et al.

It is certified that error appears in the above-identified patent and that said Letters Patent is hereby corrected as shown below:

In column 5, line 44, after "Fastener" please insert --54--.

IN THE CLAIMS

In claim 6, line 3, please delete "cable" and substitute therefor --cables--.

Signed and Sealed this

Twelfth Day of January, 1993

Attest:

DOUGLAS B. COMER

Attesting Officer     Acting Commissioner of Patents and Trademarks